(12) United States Patent
Michael

(10) Patent No.: US 9,511,001 B2
(45) Date of Patent: Dec. 6, 2016

(54) MEDICAL CABINET ACCESS BELT OPTIMIZATION SYSTEM

(71) Applicant: ARxIUM, Inc., Buffalo Grove, IL (US)

(72) Inventor: James A. Michael, Cranberry Township, PA (US)

(73) Assignee: ARxIUM, Inc., Buffalo Grove, IL (US)

( * ) Notice: Subject to any disclaimer, the term of this patent is extended or adjusted under 35 U.S.C. 154(b) by 0 days.

(21) Appl. No.: 15/072,008

(22) Filed: Mar. 16, 2016

(65) Prior Publication Data

US 2016/0193115 A1 Jul. 7, 2016

Related U.S. Application Data

(63) Continuation of application No. 14/256,740, filed on Apr. 18, 2014, now Pat. No. 9,345,644, which is a continuation of application No. 13/087,070, filed on Apr. 14, 2011, now Pat. No. 8,744,621, which is a continuation-in-part of application No. 13/040,931, filed on Mar. 4, 2011, now Pat. No. 9,121,197, which is a continuation-in-part of application No. 13/032,753, filed on Feb. 23, 2011, now Pat. No. 8,588,966, which is a continuation-in-part of application No. 12/351,679, filed on Jan. 9, 2009, now Pat. No. 8,103,379.

(51) Int. Cl.

| | |
|---|---|
| *G07F 17/00* | (2006.01) |
| *A61J 7/00* | (2006.01) |
| *E05B 47/00* | (2006.01) |
| *E05B 65/46* | (2006.01) |
| *G06F 19/00* | (2011.01) |

(Continued)

(52) U.S. Cl.
CPC .............. *A61J 7/0084* (2013.01); *A47B 88/20* (2013.01); *E05B 47/00* (2013.01); *E05B 65/462* (2013.01); *G06F 19/3462* (2013.01); *G07F 11/18* (2013.01); *G07F 11/60* (2013.01); *G07F 11/62* (2013.01); *G07F 17/0092* (2013.01); *E05B 2047/0094* (2013.01)

(58) Field of Classification Search
CPC .................................................... G07F 17/0092
USPC .................. 221/122, 133; 700/236, 242, 243
See application file for complete search history.

(56) References Cited

U.S. PATENT DOCUMENTS

| 3,682,113 A | 8/1972 | McClellan et al. |
| 4,057,145 A | 11/1977 | Wray et al. |

(Continued)

FOREIGN PATENT DOCUMENTS

| EP | 0488548 | 3/1992 |
| JP | H 10-501143 A | 2/1998 |

(Continued)

OTHER PUBLICATIONS

U.S. Appl. No. 14/969,370, filed Dec. 15, 2015, Arxium, Inc.

(Continued)

*Primary Examiner* — Timothy Waggoner

(74) *Attorney, Agent, or Firm* — Reinhart Boerner Van Deuren s.c.

(57) ABSTRACT

A cabinet for securely storing items includes a drawer enclosure, a drawer, a cover, an electric actuator, and a switch. The drawer is slidable at least partially into and out of the enclosure, and includes a compartment. A cover which is configured as a metal belt is designed to selectively block access to the compartments of the drawer when the cover is in a first configuration, and to allow access to the compartment when the cover is in a second configuration. The electric actuator is designed to move the cover from the first configuration to the second configuration in one of two directions. The actuator selects the direction to reduce the time required to make such movement.

5 Claims, 14 Drawing Sheets

(51) Int. Cl.
  *G07F 11/18* (2006.01)
  *G07F 11/60* (2006.01)
  *G07F 11/62* (2006.01)
  *A47B 88/20* (2006.01)

(56) References Cited

U.S. PATENT DOCUMENTS

| | | |
|---|---|---|
| 4,267,942 A | 5/1981 | Wick, Jr. et al. |
| 4,763,810 A | 8/1988 | Christiansen |
| 4,785,969 A | 11/1988 | McLaughlin |
| 4,865,404 A | 9/1989 | Harper |
| 4,915,205 A | 4/1990 | Reid et al. |
| 4,927,051 A | 5/1990 | Falk et al. |
| 4,941,570 A | 7/1990 | Kruger et al. |
| 5,014,875 A * | 5/1991 | McLaughlin ....... G07F 17/0092 221/122 |
| 5,046,455 A | 9/1991 | Christiansen et al. |
| 5,087,107 A | 2/1992 | Fumanelli |
| 5,222,789 A | 6/1993 | Yoshikawa |
| 5,246,136 A | 9/1993 | Loidl |
| 5,255,971 A | 10/1993 | Aisley |
| 5,259,668 A | 11/1993 | Teufel et al. |
| 5,263,596 A | 11/1993 | Williams |
| 5,282,678 A | 2/1994 | Teufel et al. |
| 5,322,365 A | 6/1994 | Teufel et al. |
| 5,346,297 A | 9/1994 | Colson, Jr. et al. |
| 5,377,864 A | 1/1995 | Blechl et al. |
| 5,404,384 A | 4/1995 | Colburn et al. |
| 5,405,048 A | 4/1995 | Rogers et al. |
| 5,445,294 A | 8/1995 | Gardner et al. |
| 5,445,295 A | 8/1995 | Brown |
| 5,460,294 A | 10/1995 | Williams |
| 5,467,266 A | 11/1995 | Jacobs et al. |
| 5,520,450 A | 5/1996 | Colson, Jr. et al. |
| 5,533,079 A | 7/1996 | Colburn et al. |
| 5,713,485 A | 2/1998 | Liff et al. |
| 5,724,764 A | 3/1998 | Alsup |
| 5,743,607 A | 4/1998 | Teufel et al. |
| 5,745,366 A | 4/1998 | Higham et al. |
| 5,790,409 A | 8/1998 | Fedor et al. |
| 5,797,515 A | 8/1998 | Liff et al. |
| 5,805,456 A | 9/1998 | Highan et al. |
| 5,839,257 A | 11/1998 | Soderstrom et al. |
| 5,848,593 A | 12/1998 | McGrady et al. |
| 5,883,806 A * | 3/1999 | Meador ................ A61G 12/001 220/260 |
| 5,905,653 A | 5/1999 | Higham et al. |
| 5,912,818 A | 6/1999 | McGrady et al. |
| 5,927,540 A * | 7/1999 | Godlewski ............. E05B 65/46 221/103 |
| 5,961,036 A | 10/1999 | Michael et al. |
| 6,011,999 A | 1/2000 | Holmes |
| 6,019,249 A | 2/2000 | Michael et al. |
| 6,068,156 A | 5/2000 | Liff et al. |
| 6,073,834 A | 6/2000 | Michael et al. |
| 6,109,774 A | 8/2000 | Holmes et al. |
| 6,116,461 A | 9/2000 | Broadfield et al. |
| 6,151,536 A | 11/2000 | Arnold et al. |
| 6,163,737 A | 12/2000 | Fedor et al. |
| 6,170,230 B1 | 1/2001 | Chudy et al. |
| 6,170,929 B1 | 1/2001 | Wilson et al. |
| 6,175,779 B1 | 1/2001 | Barrett |
| 6,256,967 B1 | 7/2001 | Hebron et al. |
| 6,338,007 B1 | 1/2002 | Broadfield et al. |
| 6,348,864 B1 | 2/2002 | Lin |
| 6,401,991 B1 | 6/2002 | Eannone |
| 6,427,865 B1 | 8/2002 | Stillwell et al. |
| 6,471,089 B2 | 10/2002 | Liff et al. |
| 6,502,718 B2 | 1/2003 | Fitzgerald et al. |
| 6,532,399 B2 * | 3/2003 | Mase ................ E05B 19/0005 221/154 |
| 6,564,121 B1 | 5/2003 | Wallace et al. |
| 6,581,798 B2 | 6/2003 | Liff et al. |
| 6,594,549 B2 | 7/2003 | Siegel |
| 6,609,047 B1 | 8/2003 | Lipps |
| 6,625,952 B1 | 9/2003 | Chudy et al. |
| 6,650,964 B2 | 11/2003 | Spano, Jr. et al. |
| 6,658,322 B1 | 12/2003 | Frederick et al. |
| 6,662,081 B1 | 12/2003 | Jacober et al. |
| 6,735,497 B2 | 5/2004 | Wallace et al. |
| 6,742,671 B2 | 6/2004 | Hebron et al. |
| 6,746,091 B2 | 6/2004 | Friar et al. |
| 6,760,643 B2 | 7/2004 | Lipps |
| 6,775,591 B1 | 8/2004 | Shoenfeld |
| 6,776,304 B2 | 8/2004 | Liff et al. |
| 6,776,306 B1 | 8/2004 | Michael et al. |
| 6,785,589 B2 | 8/2004 | Eggenberger et al. |
| 6,788,997 B1 | 9/2004 | Frederick |
| 6,814,254 B2 | 11/2004 | Liff et al. |
| 6,814,255 B2 | 11/2004 | Liff et al. |
| 6,847,861 B2 | 1/2005 | Lunak et al. |
| 6,895,304 B2 | 5/2005 | Spano, Jr. et al. |
| 6,902,083 B1 | 6/2005 | Michael et al. |
| 6,963,791 B1 | 11/2005 | Frederick et al. |
| 6,975,922 B2 | 12/2005 | Duncan et al. |
| 6,985,797 B2 | 1/2006 | Spano, Jr. et al. |
| 6,996,455 B2 | 2/2006 | Eggenberger et al. |
| 6,997,377 B2 | 2/2006 | Washington et al. |
| 7,006,893 B2 | 2/2006 | Hart et al. |
| 7,010,389 B2 | 3/2006 | Lanak et al. |
| 7,040,504 B2 | 5/2006 | Broadfield et al. |
| 7,044,569 B1 | 5/2006 | Relyea et al. |
| 7,048,142 B1 | 5/2006 | Michael et al. |
| 7,052,097 B2 | 5/2006 | Meek, Jr. et al. |
| 7,072,737 B2 | 7/2006 | Lunak et al. |
| 7,077,286 B2 | 7/2006 | Shows et al. |
| 7,151,982 B2 | 12/2006 | Liff et al. |
| 7,152,441 B2 | 12/2006 | Friar et al. |
| 7,228,200 B2 | 6/2007 | Baker et al. |
| 7,258,241 B2 | 8/2007 | Reid |
| 7,258,249 B1 | 8/2007 | Frederick et al. |
| 7,262,698 B1 | 8/2007 | Frederick et al. |
| 7,263,410 B1 | 8/2007 | Frederick et al. |
| 7,286,900 B1 | 10/2007 | Frederick et al. |
| 7,293,672 B2 | 11/2007 | Mori et al. |
| 7,293,673 B2 | 11/2007 | Savage et al. |
| 7,349,858 B1 | 3/2008 | McGrady et al. |
| 7,395,945 B2 | 7/2008 | Godlewski |
| 7,426,425 B2 | 9/2008 | Meek, Jr. et al. |
| 7,427,002 B2 | 9/2008 | Liff et al. |
| 7,427,022 B2 | 9/2008 | Yokota et al. |
| 7,434,704 B2 | 10/2008 | Yuyama et al. |
| 7,463,947 B1 | 12/2008 | Frederick et al. |
| 7,464,832 B2 | 12/2008 | Lee |
| 7,467,093 B1 | 12/2008 | Newton et al. |
| 7,502,666 B2 | 3/2009 | Siegel et al. |
| 7,515,988 B1 | 4/2009 | Frederick et al. |
| 7,596,427 B1 | 9/2009 | Frederick et al. |
| 7,630,789 B2 | 12/2009 | Broadfield et al. |
| 7,630,791 B2 | 12/2009 | Nguyen et al. |
| 7,685,026 B1 | 3/2010 | McGrady et al. |
| 7,689,316 B1 | 3/2010 | Frederick et al. |
| 7,689,317 B2 | 3/2010 | McGrady et al. |
| 7,719,420 B2 | 5/2010 | Christie et al. |
| 7,726,095 B2 | 6/2010 | Yuyama |
| 7,747,190 B2 | 6/2010 | Kimura et al. |
| 7,751,932 B1 | 7/2010 | Fedor et al. |
| 7,782,198 B2 | 8/2010 | Crockett |
| 7,805,216 B2 | 9/2010 | Shows et al. |
| 7,806,488 B2 * | 10/2010 | Hannan ................ A47B 88/20 312/209 |
| 7,823,993 B2 | 11/2010 | Ostrowski |
| 7,848,846 B2 | 12/2010 | Uema et al. |
| 7,991,507 B2 | 8/2011 | Liff et al. |
| 8,068,932 B2 | 11/2011 | Kirzinger |
| 8,096,628 B2 | 1/2012 | Ostrowski |
| 8,103,379 B2 | 1/2012 | Biba et al. |
| 8,180,484 B2 | 5/2012 | Baker et al. |
| 8,197,017 B2 | 6/2012 | Rahilly |
| 8,231,749 B2 | 7/2012 | Dent et al. |
| 8,234,008 B2 * | 7/2012 | Weber ................ A47B 67/02 221/130 |
| 8,262,174 B2 | 9/2012 | Rahilly |
| 8,335,588 B2 | 12/2012 | Rahilly et al. |

(56) References Cited

U.S. PATENT DOCUMENTS

| | | |
|---|---|---|
| 8,423,180 B1 | 4/2013 | Frederick et al. |
| 8,517,215 B2 | 8/2013 | Shafir et al. |
| 8,588,966 B2 | 11/2013 | Michael |
| 8,744,621 B2 | 6/2014 | Michael |
| 9,111,408 B2 | 8/2015 | Biba et al. |
| 9,117,016 B2 | 8/2015 | Carson et al. |
| 9,121,197 B2 | 9/2015 | Michael |
| 9,122,783 B2 | 9/2015 | Carson et al. |
| 9,243,427 B2 | 1/2016 | Weber et al. |
| 9,245,405 B2 | 1/2016 | Michael |
| 9,345,644 B2 * | 5/2016 | Michael ................ E05B 47/00 |
| 2001/0019065 A1 | 9/2001 | William et al. |
| 2001/0044731 A1 | 11/2001 | Coffman et al. |
| 2002/0130135 A1 * | 9/2002 | Fitzgerald ................ G07F 5/26 221/92 |
| 2003/0088333 A1 | 5/2003 | Liff et al. |
| 2003/0201697 A1 | 10/2003 | Richardson |
| 2004/0026442 A1 | 2/2004 | Hutchinson |
| 2004/0104652 A1 | 6/2004 | Holmes et al. |
| 2004/0134043 A1 | 7/2004 | Uema et al. |
| 2004/0158350 A1 | 8/2004 | Ostergaard et al. |
| 2005/0145644 A1 | 7/2005 | Mori et al. |
| 2006/0079994 A1 | 4/2006 | Chu et al. |
| 2006/0125356 A1 | 6/2006 | Meek, Jr. et al. |
| 2006/0151517 A1 | 7/2006 | Varis |
| 2006/0175942 A1 | 8/2006 | Meek et al. |
| 2006/0197419 A1 | 9/2006 | Sorensen |
| 2006/0277269 A1 | 12/2006 | Dent et al. |
| 2007/0023193 A1 | 2/2007 | King |
| 2007/0078562 A1 | 4/2007 | Park, IV |
| 2007/0208598 A1 | 9/2007 | McGrady et al. |
| 2007/0262147 A1 | 11/2007 | Braun et al. |
| 2007/0283733 A1 | 12/2007 | Ratkus et al. |
| 2008/0065264 A1 | 3/2008 | Omura |
| 2008/0129171 A1 | 6/2008 | Greiner |
| 2008/0190953 A1 | 8/2008 | Mallett et al. |
| 2009/0015116 A1 | 1/2009 | Arceta et al. |
| 2009/0055018 A1 | 2/2009 | Meek, Jr. et al. |
| 2009/0108016 A1 | 4/2009 | Brown et al. |
| 2009/0114672 A1 | 5/2009 | Schifman et al. |
| 2009/0138122 A1 | 5/2009 | Wagner |
| 2009/0198347 A1 * | 8/2009 | Kirzinger ................ G07F 11/62 700/1 |
| 2010/0079240 A1 | 4/2010 | Higham |
| 2010/0176699 A1 | 7/2010 | Biba et al. |
| 2010/0228392 A1 | 9/2010 | Braun |
| 2011/0012374 A1 | 1/2011 | Ostrowski |
| 2011/0015782 A1 | 1/2011 | Chudy et al. |
| 2011/0140831 A1 | 6/2011 | Michael |
| 2011/0156560 A1 | 6/2011 | Michael |
| 2011/0266929 A1 | 11/2011 | Michael |
| 2014/0222196 A1 | 8/2014 | Michael |
| 2015/0305500 A1 | 10/2015 | Biba et al. |
| 2015/0320212 A1 | 11/2015 | Michael |

FOREIGN PATENT DOCUMENTS

| | | |
|---|---|---|
| JP | 2001275766 | 10/2001 |
| JP | 2003509084 | 3/2003 |
| JP | 2005143401 | 6/2005 |
| JP | 2005287609 | 10/2005 |
| JP | 2007126270 | 5/2007 |
| KR | 10/0963597 | 6/2010 |
| WO | WO 9520804 A | 8/1995 |
| WO | WO 00/32073 | 6/2000 |
| WO | WO 2010-080660 | 7/2010 |

OTHER PUBLICATIONS

English language machine translation of JP 2007126270 provided by foreign associate on Dec. 27, 2013, 13 pages.

International Search Report and Written Opinion for International Application No. PCT/US2012/026156, mail date Dec. 10, 2012, 9 pages.

International Search Report and Written Opinion for International Application No. PCT/US2009/069432, mail date Aug. 27, 2010, 6 pages.

International Search Report and Written Opinion for International Application No. PCT/US2012/025673, mail date Dec. 26, 2012, 10 pages.

International Search Report and Written Opinion for International Application No. PCT/US2012/030922, mailed on Oct. 18, 2012, 12 pages.

Japanese Patent Office, Office Action regarding application 2015-040191, Jan. 19, 2016.

* cited by examiner

US 9,511,001 B2

MEDICAL CABINET ACCESS BELT OPTIMIZATION SYSTEM

CROSS-REFERENCE TO RELATED APPLICATIONS

This application is a continuation of prior U.S. patent application Ser. No. 14/256,740, filed on Apr. 18, 2014, which is a continuation of U.S. patent application Ser. No. 13/087,070, now U.S. Pat. No. 8,744,621, filed on Apr. 14, 2011, which is a continuation-in-part of prior U.S. patent application Ser. No. 13/040,931, now U.S. Pat. No. 9,121,197, filed on Mar. 4, 2011, which is a continuation-in-part of prior U.S. patent application Ser. No. 13/032,753, now U.S. Pat. No. 8,588,966, filed on Feb. 23, 2011, which is a continuation-in-part of prior U.S. patent application Ser. No. 12/351,679, now U.S. Pat. No. 8,103,379, filed Jan. 9, 2009, all of which are incorporated herein by reference in their entirety.

BACKGROUND

The present disclosure relates generally to the field of cabinetry for storing medical supplies. More specifically, the present disclosure relates to a cabinet system for providing security related to stored items, such as medical supplies.

SUMMARY

One embodiment of the invention relates to a secured drawer for a supply cabinet. The secured drawer includes a plurality of compartments which are arranged end to end from a first end to a second end. There is a first roller supported at the first end and a second roller supported at the second end. There is a belt which has a first opening and a second opening larger than the first opening. The belt is moveably supported by the rollers and moveably aligns at least one of the openings with one of the compartments while restricting access to at least one of the compartments. A belt actuator is operable to selectively move the belt in either a first direction or a second direction to change access from one of the compartments to another of the compartments. The actuator is configured to move the belt in the direction which minimizes the time required to change access from one compartment to another.

Another embodiment of the invention provides for a storage system for securely storing items therein. The storage system includes a drawer unit having a plurality of compartments formed therein. A belt is rotatably disposed about the compartments of the drawer unit and has at least a first opening formed therein. The belt is rotatable in either a clockwise or counter-clockwise direction to align the opening with a compartment to provide access to at least one of the plurality of compartments while restricting access to at least one of the plurality of compartments. A belt actuator selectively rotates the belt to provide access to one of the plurality of compartments. The direction of rotation of the belt actuator is selected to minimize the time required to move the opening to provide access to compartments.

In yet another embodiment of the invention is a storage system for securely storing items therein. The storage system includes a drawer unit comprising a plurality of compartments formed therein. There is cover comprising a first opening and a second opening formed therein, wherein the first opening has a wider area than the second opening. An actuator selectively moves the cover during operation use of the system. A controller in communication with the actuator directs the actuator to move the cover such that either the first opening or the second opening is aligned with a designated compartment, depending upon the size of the designated compartment.

In still another embodiment of the invention, there is a storage system for securely storing items therein. The storage system includes a drawer unit comprising a plurality of compartments formed therein. A cover covering the plurality of compartments includes an opening that may be selectively aligned with a designated compartment to allow access thereto. An actuator selectively moves the belt during operational use of the system. A sensor is configured to detect a position of the cover. A controller in communication with the actuator and the sensor receives data from the sensor that is representative of the position of the cover relative to the drawer unit. The controller directs the actuator to move the cover such that the opening is aligned with the designated compartment during operation use of the system.

BRIEF DESCRIPTION OF THE FIGURES

The present invention will become more fully understood from the following detailed description, taken in conjunction with the accompanying figures, wherein like reference numerals refer to like elements, in which.

DETAILED DESCRIPTION

Before turning to the figures, which illustrate the exemplary embodiments in detail, it should be understood that the present invention is not limited to the details or methodology set forth in the description or illustrated in the figures. It should also be understood that the terminology is for the purpose of description only and should not be regarded as limiting.

Access to medical items, such as medications, medical instruments, medicinal applicators, healthcare-related articles, or other items, may be controlled by a storage cabinet system (e.g., medication cabinetry) designed to inhibit misuse, mistaken use, and theft of such items. The cabinet system may be used by doctors, nurses, technicians, pharmacists, and others to store and controllably distribute the items. In at least one embodiment disclosed herein, a cabinet system provides selective access to the items, which are stored in one or more drawer units of the cabinet system. The cabinet system is sensitive to unauthorized attempts to access the contents of the one or more drawer units, and stores data representative of such attempts, whether or not the attempts are successful.

Figure 1:
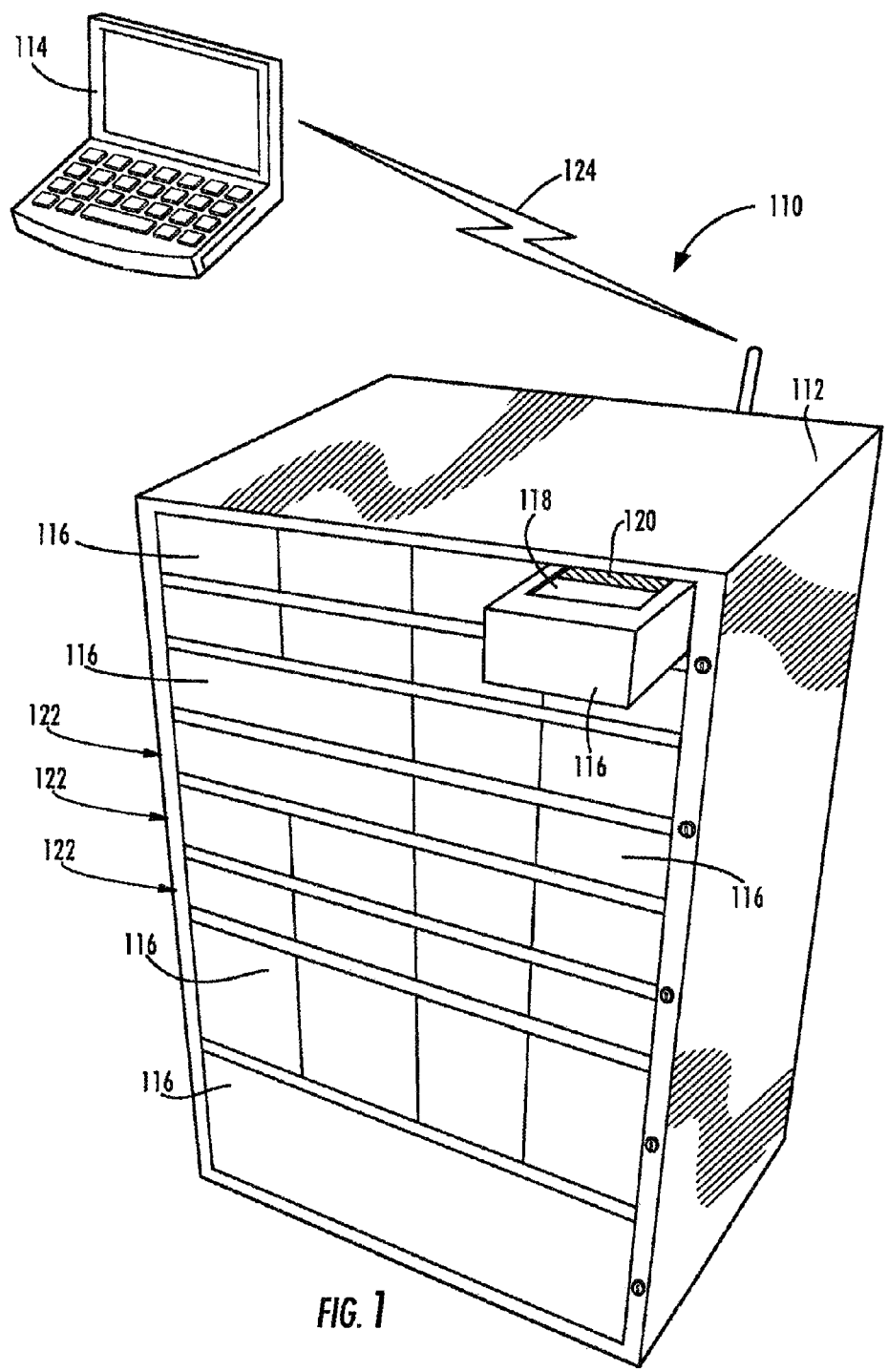
FIG. 1 is a perspective view of a cabinet system according to an exemplary embodiment of the invention.
Figure 3:
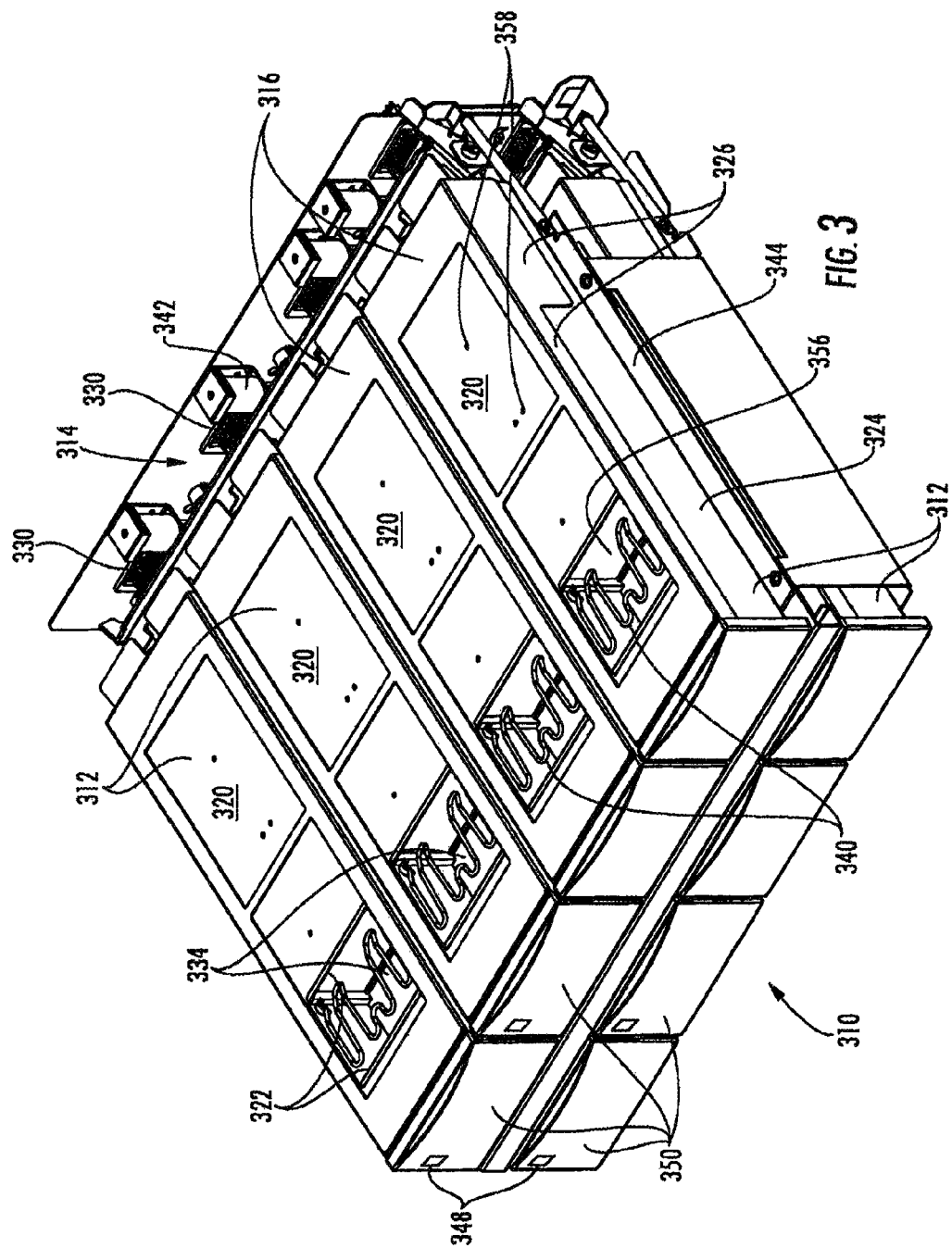
FIG. 3 is a perspective view of a portion of a cabinet system according to an exemplary embodiment of the invention.

Referring to FIG. 1, a cabinet system 110 (e.g., dispensing station) includes a cabinet housing 112 (e.g., frame), a controller 114, and one or more drawer units 116 (e.g., secure drawers with lids). According to an exemplary embodiment, the drawer units 116 of the cabinet system 110 are arranged in one or more vertically-stacked rows 122, each row 122 including one or more drawer units 116. The drawer units 116 of the rows 122 may be uniform in size (see, e.g., assembly 310 of drawer units 312 as shown in FIG. 3), or may include a variety of different sizes and relative capacities.

Figure 2:
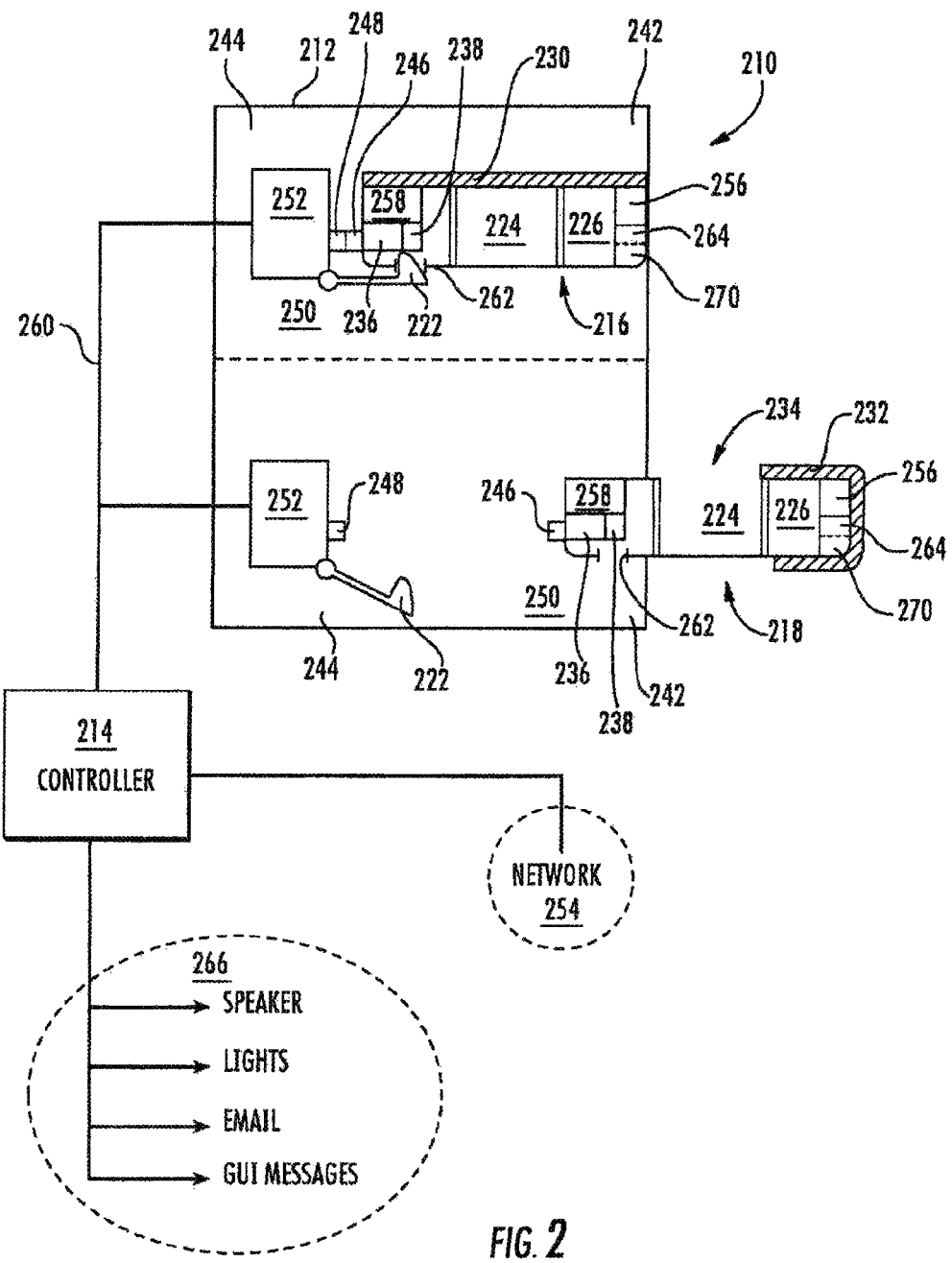
FIG. 2 is a schematic diagram of a cabinet system according to another exemplary embodiment of the invention.

One or more of the drawer units 116 are configured to be releasably locked at least partially within the cabinet housing 112 by a locking mechanism (see, e.g., locking mechanism 222 as shown in FIG. 2). Locking of the drawer unit 116 within the cabinet housing 112 may inhibit unauthorized access to contents of the drawer unit 116, and/or unauthorized removal of the entire drawer unit 116. However, when the locking mechanism is released, the drawer unit 116 may be slid relative to the cabinet housing 112, such as pulled partially or fully out of the cabinet housing 112.

Still referring to FIG. 1, each drawer unit 116 includes a storage compartment 118 (e.g., container) and a cover 120 coupled thereto. The storage compartment 118 is designed to securely store one or more items therein, such as medical supplies, and the cover 120 is designed to move to an open configuration and a closed configuration. While in a closed configuration, the cover 120 is designed to limit access to the items of the storage compartment 118. However, when the cover 120 is in the open configuration and the drawer unit 116 has been sufficiently slid from the cabinet housing 112, contents of the storage compartment 118 may be accessible for removal from the drawer unit 116.

In FIG. 1, the controller 114 is shown to include a computer terminal (e.g., laptop computer). The controller 114 is in communication (e.g., wireless communication 124 or over a wired network) with at least one of the cabinet housing 112 and/or one of the drawer units 116. According to an exemplary embodiment, the controller 114 is configured to control operation of the locking mechanism, so as to control the release of the locking mechanism and correspondingly release the drawer unit 116 with respect to the cabinet housing 112. In some embodiments, the controller 114 is further configured to control movement of the cover 120, such as to move the cover 120 from the closed configuration to the open configuration, and/or visa versa.

According to an exemplary embodiment, at least one of the drawer units 116 includes a tamper detection system. After the drawer unit 116 has been released from the locking mechanism and the cover 120 is in the open configuration relative to one of several compartments, the drawer unit 116 is sensitive to additional movements of the cover 120. For example, if a would-be thief attempts to manually force movement of the cover 120 to gain unauthorized access to additional compartments, a component(s) (e.g., sensor) of the drawer unit 116 provides notice of the attempt—regardless of whether the attempt was successful or not. In some embodiments, the component generates a signal that triggers an alarm. In some embodiments, the signal is stored in memory coupled to the drawer unit 116, and/or communicated to the controller 114 to be analyzed and possibly further communicated. In other contemplated embodiments, the memory may be coupled to the cabinet housing 112 or to the controller 114.

Referring now to FIG. 2, a cabinet system 210 includes a cabinet housing 212, a controller 214, an upper drawer unit 216, and a lower drawer unit 218. According to an exemplary embodiment, each drawer unit 216, 218 includes at least a first storage compartment 224 and a second storage compartment 226. Each storage compartment 224, 226 is configured to store (e.g., hold, contain) one or more items. A locking mechanism 222 is configured to releasably lock each drawer unit 216, 218 at least partially within the cabinet housing 212—for example, substantially within the cabinet housing 212, but with an end (e.g., face, handle, extensions) of each drawer unit 216, 218 extending from the cabinet housing 212.

As shown in FIG. 2, a cover 230 of the upper drawer unit 216 is in a closed configuration, blocking access to contents of the storage compartments 224, 226 thereof. A cover 232 of the lower drawer unit 218 is in an open configuration relative to the first storage compartment 224 thereof, where the cover 232 is clear of an opening 234 (e.g., open end, top) of the first storage compartment 224. As such, items stored in the first storage compartment 224 of the lower drawer unit 218 may be accessed (e.g., removed, added, replaced, used). However, items stored in the second storage compartment 226 of the lower drawer unit 218 are inaccessible as shown in FIG. 2, because the cover 232 is in a closed configuration relative to the second storage compartment 226 blocking access thereto.

According to an exemplary embodiment, the cabinet housing 212 includes a vertical arrangement of enclosures 250 (e.g., bays, openings, etc.). Each enclosure 250 includes a rear portion 244 and a front portion 242. The front portion 242 of each enclosure 250 is configured to receive at least one drawer unit 216, 218 inserted through an opening and slid within the cabinet housing 212 toward the rear portion 244. Proximate to the rear portion 244 of each enclosure 250, the cabinet housing 212 includes a connector 248 (e.g., port, interface, link, coupling) for receiving a complementary connector 246 coupled each drawer unit 216, 218.

Coupling of the connectors 246, 248 allows for power and/or data communication between the controller 214 and the drawer units 216, 218, where the controller 214 is linked to the enclosures 250 of the cabinet housing 212 by wire 260. According to an exemplary embodiment, the connectors 246, 248 may be disconnected from each other when each drawer unit 216, 218 is slid away from the rear portion 244 of the enclosure 250, and may be reconnected when the respective drawer unit 216, 218 is then slid back to the rear portion 244 of the enclosure 250, reconnecting the connectors 246, 248.

According to an exemplary embodiment, at least one of the connectors 246, 248 includes one or more spring-loaded pins (see, e.g., pins 330 as shown in FIG. 3) and the other of the connectors 246, 248 includes one or more complementary ports configured to receive the pins. The pins may be pulled from the ports as the drawer units 216, 218 are slid away from the rear portion 244 of the cabinet housing 212, and then reconnected to the ports when the drawer units 216, 218 are slid back. In other contemplated embodiments, the controller 214 and each drawer unit 216, 218 remain in continuous communication (e.g., wired or wireless communication), even when the drawer units 216, 218 are slid partially out of each enclosure 250.

In various embodiments the controller 214 may include a broad range of control devices, such as a general purpose processor, application-specific integrated circuitry, a digital control interface mounted directly to the cabinet housing, a handheld remote control, a network of computers hard-wired to the cabinet system 210, or any other collection of circuitry components configured to conduct calculations or to facilitate the activities described herein. In contemplated embodiments, the controller 214 may be in wired or wireless communication, fiber optic communication, communication via mechanical linkage, or otherwise coupled to at least one of the cabinet housing 212 and/or one of the drawer units 216, 218 of the cabinet system 210. The controller 214 of FIG. 2 may also be linked to a network 254, such as an arrangement of hospital computers coupled to the internet or databases containing medical item information, medical personnel authorization information, or patient-related care information.

The controller 214 is configured to operate the locking mechanism 222 for each drawer unit 216, 218 via an actuator 252, such as an electric solenoid coupled to the locking mechanism 222. In various contemplated embodiments, the locking mechanism 222 includes at least one of a latch, a pin, a hook, a sliding bar, an interfering member, or another type of locking mechanisms, such as other remotely-controllable locking mechanisms that are commercially available. While the locking mechanism 222 in FIG. 2 is shown to selectively lock an underside 262 of each drawer unit 216, 218 to the rear portion 244 of each enclosure 250, it is contemplated that in other embodiments a locking mechanism may be configured to selectively lock any portion of each drawer unit 216, 218 to any other portion of the cabinet system 210.

The controller 214 is further configured to operate the covers 230, 232 of the drawer units 216, 218, such as to instruct one or more of the covers 230, 232 to move to an open configuration relative to one or more of the respective compartments 224, 226. According to an exemplary embodiment, movement of the covers 230, 232 may occur while each drawer unit 216, 218 is in one of the enclosures 250, such that the items of the drawer units 216, 218 may be then accessible when the drawer units 216, 218 are sufficiently slid out of the cabinet housing 212. In some embodiments, the covers 230, 232 are configured to move forward and backward (e.g., bi-directionally) relative to the compartments 224, 226.

The controller 214 is still further configured to operate a lock 256 coupled to each cover 230, 232. The lock 256 may be used to fix the respective cover 230, 232 in a particular configuration, orientation, or position when the corresponding drawer unit 216, 218 is slid away from the rear portion 244 of the cabinet housing 212. The lock 256 may include, but is not limited to a solenoid configured to engage locking holes in the covers 230, 232 (see, e.g., track 338 with perforations 346 as shown in FIG. 5), a spring-biased latch configured to engage each cover 230, 232 when the respective drawer unit 216, 218 is removed from the cabinet housing 212, and/or a high-ratio gear reduction (e.g., high-reduction gear box) of an electric motor 258 or other actuator used for controllably moving the covers 230, 232, where with the electric motor 258 stopped, the gear reduction is difficult to manually overcome. In still other embodiments the covers 230, 232 may be braked or locked by a motor brake or by reversing the polarity of the motor.

Still referring to FIG. 2, each drawer unit 216, 218 is coupled to an electronic memory 236 and a power source 238 for the electronic memory 236. Preferably, memory 236 and power source 238 are physically supported by their respective drawer units to move with the drawer units when they are moved. In various contemplated embodiments the electronic memory 236 may store data in a variety of states, such as volatile, non-volatile, random-access memory, read-only memory, solid states, and the like. The electronic memory 236 is configured to store (e.g., record, retain, hold) data associated with movement of the covers 230, 232. In some embodiments, the electronic memory 236 stores when the covers 230, 232 are directed to move by the controller 214, and/or when the covers 230, 232 are manually forced to move, such during an attempted theft of items stored in the cabinet system 210. In some embodiments, the electronic memory 236 stores such data regardless of whether the covers 230, 232 are fully moved to an open or closed configuration.

In some embodiments, the electronic memory 236 is coupled to a clock and stores the time, date, and duration of movements of the covers 230, 232 and/or relative configurations, positions, and orientations of the covers 230, 232 (e.g., data such as: 'compartment 226 of drawer unit 218 was open from 18:00:31 to 18:17:09 hours on Month, Day, Year). In other embodiments, the electronic memory 236 is configured to only store data when the covers 230, 232 have been manually forced to move, such as without authorization from the controller 214. Data may include data representative of one or more signals generated by encoders (e.g. magnetic or optical) which monitor cover movement, cam switches, hall effect sensors, capacitor discharge responsive to cover movement, sensor switch state change in response to unauthorized cover movement, monitoring of motor leads to detect movement of a belt-type cover. Upon reinsertion and connection of these drawers the data and/or state changes can be read and detected by the controller.

In variant contemplated embodiments, the power source 238 for the electronic memory 236 includes a battery, a power cell, a capacitor selectively charged by the controller 214, and/or other power sources, which may be coupled to each drawer unit 216, 218. Memory of events may be recorded on the electronic memory 236 and retained for download, even after the power source 238 has expired or terminated. In other embodiments, the electronic memory 236 may distinguish between authorized and unauthorized manual movements of the covers 230, 232. For example, the electronic memory may record when an authorized user is implementing a manual key override, such as during a power outage. In still other embodiments, an unauthorized movement of the covers 230, 232 may be detected by comparing the relative position of one of the covers 230, 232 before and after a drawer unit 216, 218 has been accessed, not requiring use of the electronic memory 236 and power source 238.

According to an exemplary embodiment, data may be transferred from the electronic memory 236 to the controller 214. When the drawer units 216, 218 are linked to the controller 214, data stored on the electronic memory 236 may be downloaded by the controller (e.g., processor) and analyzed. The data may include a broad spectrum of information, including by way of non-limiting example, a time and date of access or movement, contents of a drawer unit, a form of access (e.g., authorized or unauthorized, manual or automatic, etc.), accessing individual, form of authorization (e.g., prescription code, etc.), duration of access, and other such data. Analysis of the data may be designed to determine whether an attempt had been made to access to the items within the cabinet system 210 without authorization. While the electronic memory 236 is attached to each of the drawer units 216, 218 in FIG. 2, in other contemplated embodiments electronic memory may coupled to a controller, a cabinet housing, or elsewhere in a cabinet system, and analysis of data collected regarding movement of a cover for a drawer unit may be performed in real time, substantially as the cover is moved.

Figure 4:
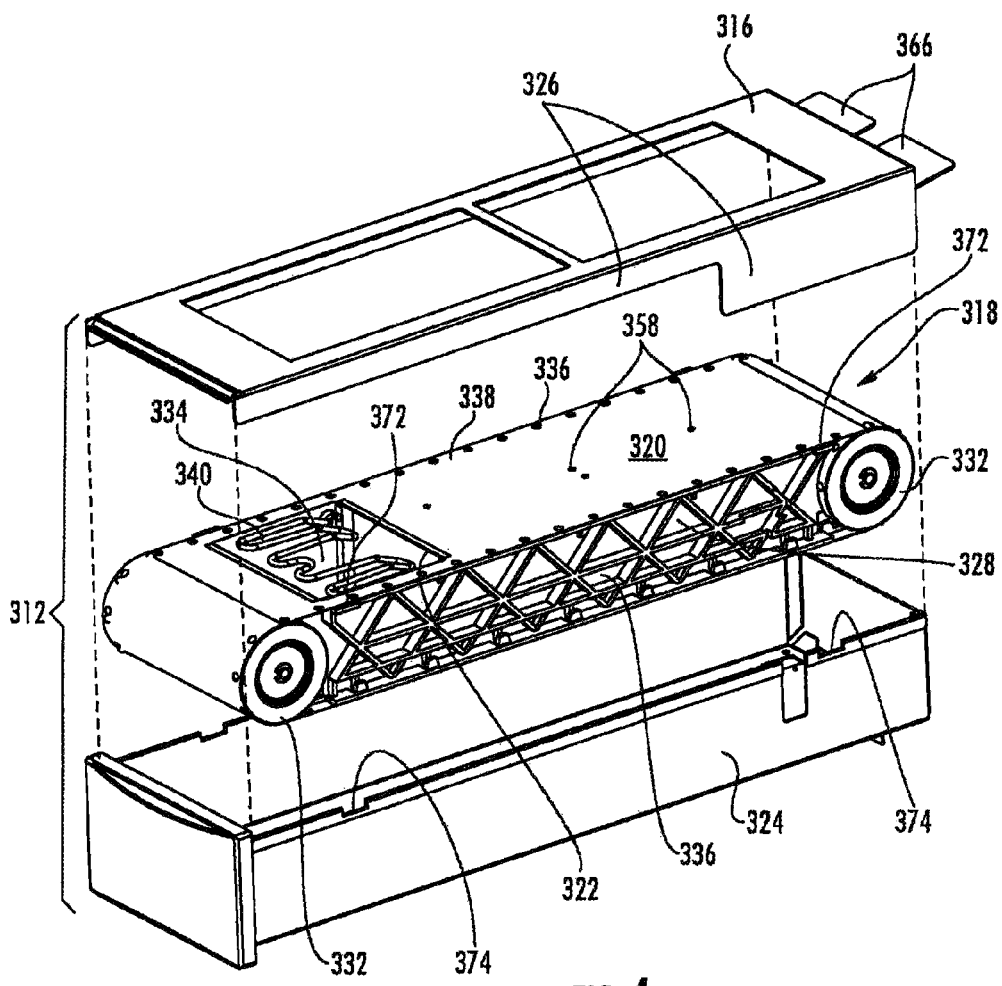
FIG. 4 is an exploded view of a drawer unit according to an exemplary embodiment of the invention.

Still referring to FIG. 2, at least one of the drawer units 216, 218 further includes a sensor 270 (e.g., photosensor, accelerometer, reed switch) coupled to the respective cover 230, 232. The sensor 270 is configured and arranged so as to directly or indirectly detect movement of the respective cover 230, 232, and to communicate the movement to the electronic memory 236 and/or to the controller 214. In some embodiments, the sensor 270 includes a potentiometer coupled to a pivot or wheel associated with movement of the cover (see, e.g., roller 332 as shown in FIG. 4). The potentiometer generates an electric signal responsive to a movement of the cover 232 relative to the compartments 224, 226. In other contemplated embodiments, the cover 230, 232 includes the electric motor 258 or other actuator configured to move the cover 230, 232 in response to instructions from the controller 214. Manual movement of the electric motor 258 (e.g., reverse operation thereof) generates an electric signal that is directed to the electronic memory 236, which records data representative of the electric signal, and in turn of the manual movement of the cover 230, 232.

According to an exemplary embodiment, each drawer unit 216, 218 includes an alarm 264. Another alarm 266 is coupled to the controller 214. In some embodiments, an electric signal generated in response to movement of one of the covers 230, 232 is also directed to at least one of the alarms 264, 266, which are configured to provide notice (e.g., alert, warn, broadcast) of unauthorized attempts to access items stored in the cabinet system 210. In some embodiments, the alarm 266 may be triggered subsequent to an unauthorized attempt, following analysis of data downloaded by the controller 214 from the electronic memory 236.

In various embodiments, the alarms 264, 266 may be visual alarms, such as flashing lights, liquid crystal displays, light-emitting diode displays, warning messages, or other such visual signals. In other embodiments, the alarms 264, 266 may be audio alarms, such as beeping, sirens, pre-recorded messages, or other such audio signals, or a combination of both visual and audio signals. In some embodiments, the alarm 266 may be a silent alarm, not intended to be noticed by the someone triggering the alarm 266, such as an electronic-mail (e-mail) message automatically transmitted, which reports an incident to an email account of at least one pre-determined person (e.g., on-call doctor, hospital security, etc.).

Referring now to FIG. 3 an assembly 310 of drawer units 312 is attached to a rear portion 314 of a cabinet housing (see, e.g., cabinet housing 112 as shown in FIG. 1). The assembly 310 includes eight drawer units 312 in two rows, where each drawer unit 312 includes a cover 320 (e.g., sliding cover, indexing belt, hinged cover, removable cover, etc.) having an opening 322 therein. Each drawer unit 312 further includes side walls 328 (FIG. 4) that form compartments 334 interior to the drawer unit 312. Restraining bars 340 are biased to hold contents of the compartments 334 within the compartments 334 when the opening 322 of the cover 320 is aligned with each compartment 334. However, the bars 340 may be manually lifted or pivoted as necessary to remove items from the compartments 334. In still other embodiments, restraining bars are not included.

A visual interface, such as a light-emitting diode (LED) display 348, is coupled to a face 350 of at least one of the drawer units 312. The LED display 348 is configured to provide a visual signal to a user of the cabinet system. According to an exemplary embodiment, the visual signal of the LED display 348 indicates that unauthorized tampering has occurred with the respective drawer unit 312. In other embodiments, the LED display 348 provides other information, such as contents of the drawer unit 312, supply status information, etc.

When the drawer units 312 are stored within the cabinet housing, a controller (see, e.g., controller 214 as shown in FIG. 2) may be in electrical or other communication with the drawer units 312. However, the rear portion 314 of the cabinet housing may also include an interlock (e.g., a switch, spring pin connection, etc.) that can break communication between the controller and the drawer units 312 when a substantial portion of each drawer unit 312 is slid from the rear portion 314 of the cabinet housing (e.g., substantial enough that an unauthorized person could grip and pull the drawer unit 312 and/or cover 320 in order to force access to the compartments 334 thereof). As shown in FIG. 3, spring-loaded connection pins 330 separate connectivity between the drawer unit 312 from the rear portion 314, cutting communication between the drawer unit 312 and the controller, upon sliding of the drawer unit 312 from the rear portion 314 of the cabinet housing.

According to an exemplary embodiment, the cover 320 forms a closure with respect to the compartments 334 of the drawer unit 312. However, the cover 320 may be moved by an electric motor 352 (see FIG. 6), repositioning the opening 322 of the cover 320 to allow controlled access to one or more of the compartments 334 and/or to form a closure with respect to other compartments 334. In some embodiments, sliding of the drawer unit 312 from the rear portion 314 of the cabinet housing stops the flow of electricity to the electric motor 352 (see FIG. 6) used to move the cover 320 interlocking the cover 320.

The rear portion 314 of the cabinet housing includes a circuitry board (e.g., firmware, programmable read-only memory (PROM)) and a releasable latch 354 (FIG. 7), both coupled to the controller. The latch 354 is configured to lock the drawer unit 312 to the rear portion 314 of the cabinet housing. An actuator 342 (e.g., solenoid, motorized pulley) may release the latch 354 when directed to do so by the controller. When unlocked, the drawer unit 312 may slide relative to the cabinet housing along a slide rail 344 that extends from the rear portion 314 of the cabinet housing.

Referring to FIG. 4 the drawer unit 312 includes a top frame 316 (e.g. cover), an insert 318, and a shell 324. The insert 318 fits within the shell 324, and the top frame 316, with flanges 326 extending therefrom, fits over the insert 318 and attaches to the shell 324. In some embodiments, the top frame 316 can be securely fastened to the shell 324 by means of a thumb screw or other fasteners, to prevent removal of the insert 318 from the shell 324.

The insert 318 includes the cover 320, a side wall 328, and rollers 332. The cover 320 may slide relative to the side wall 328 and compartments 334 via the rollers 332. In some embodiments, the insert 318 includes intermediary flanges 372 extending from the side wall 328 (or from the shell 324) to contact receiving portions 374 of the shell 324 in order to separate the cover 320 from the shell 324 during movement of the cover 320 (i.e., providing space for the cover 320 to move).

Figure 5A:
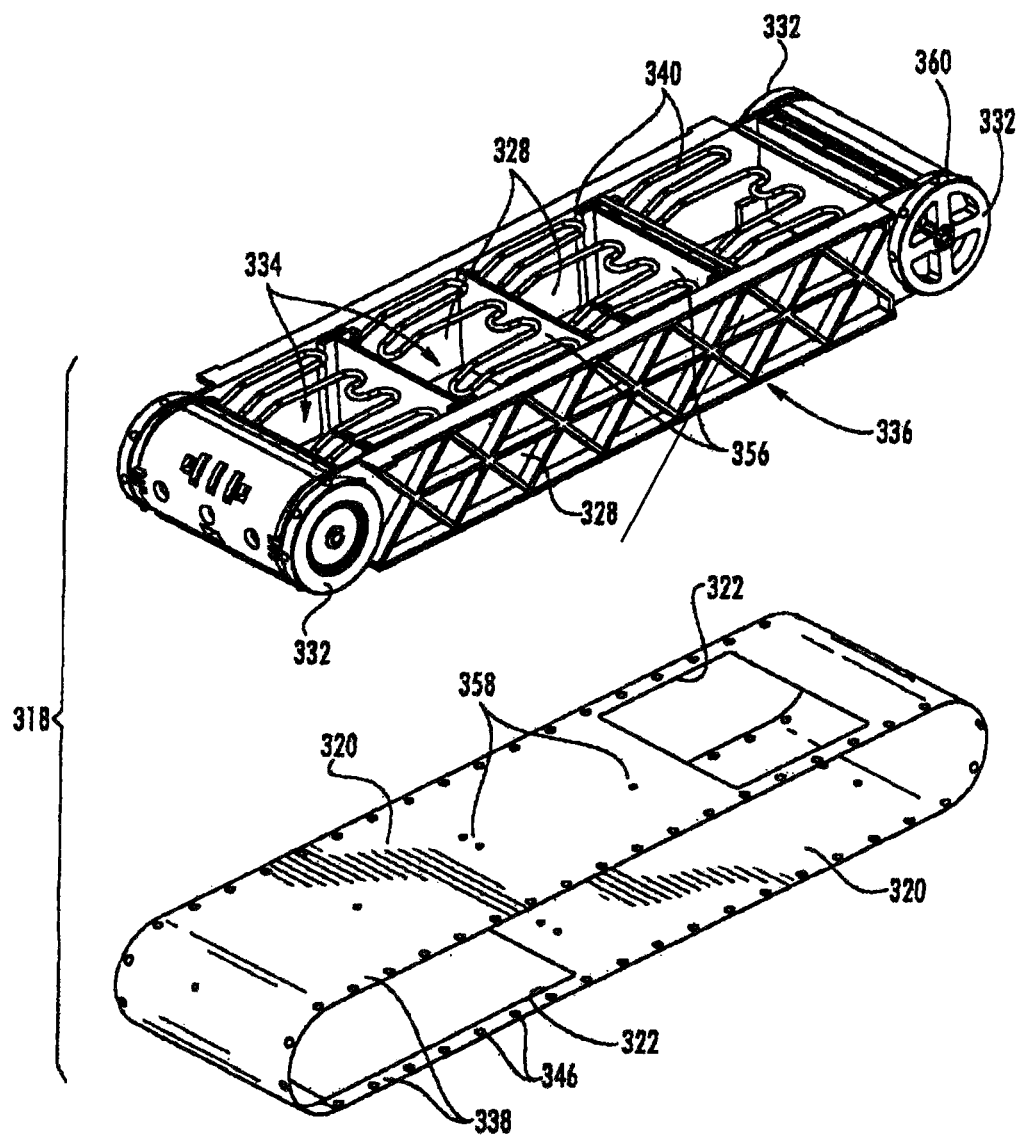
FIG. 5A is an exploded view of an insert of the drawer unit of FIG. 4.
Figure 5B:
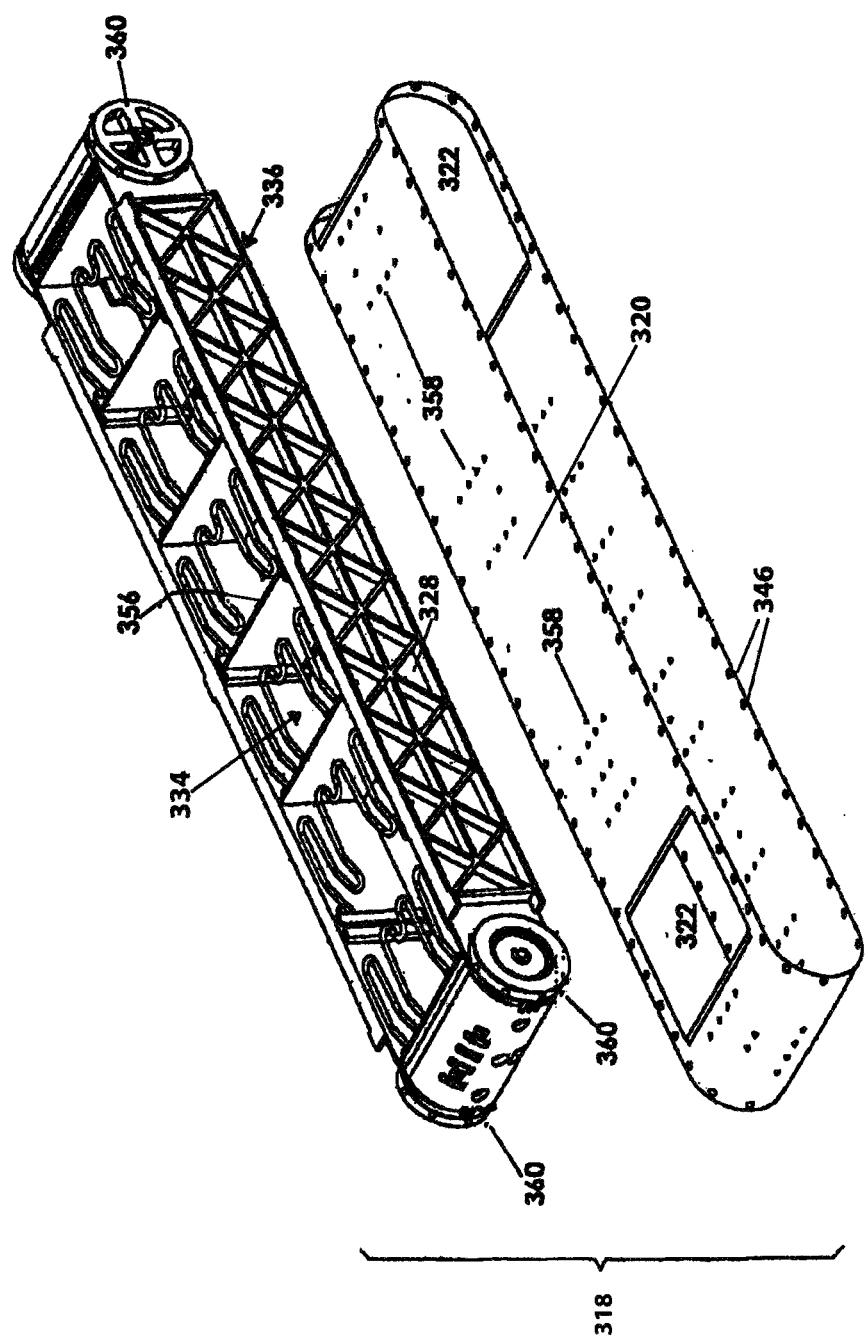
FIG. 5B is an exploded view of an alternate embodiment of an insert.

Referring now to FIGS. 5A and 5B, the insert 318 includes the cover 320 and a body 336. The body 336 includes divider walls 356 and side walls 328, which together form compartments 334. According to an exemplary embodiment, some of the divider walls 356 may be fixed while others may be removable, providing adjustable compartmentalization. In some embodiments, the insert 318 can optionally have two, three, or four compartments 334, depending upon the use of the removable divider walls 356. Items of varying sizes may be stored in differently sized compartments 334. In such embodiments, the cover 320 may include two openings 322, one configured to match a larger compartment and the other sized for a smaller compartment. Depending upon the use, there may be more than two opening sizes. The fixed divider walls 356 may be injection molded with the body 336, glued, welded, or otherwise fixed to the body 336. In other embodiments, a body of an insert may be both longer and/or deeper (or shorter and/or narrower) than the body 336 of FIG. 5. In some such embodiments, a body of an insert may include up to six compartments, with ten such inserts in a drawer assembly (cf. assembly 310 as shown in FIG. 3). FIG. 5B is similar to FIG. 5A, however, it includes more compartments. In other embodiments, inserts may include sprockets which drive both sides of a cover.

According to an exemplary embodiment, the cover 320 may be an indexing belt made of a continuous material, such as about 0.005 inch thick stainless steel sheet. Other contemplated embodiments include belts of thicker clear mylar, polycarbonate sheet, rubber, or other materials. The cover 320 is preferably made to be flexible, such that the cover 320 may bend about a portion of the insert 318, such as a roller 332. Bending of the cover 320 allows for a more-compact drawer unit design, because unused portions of the cover 320 may be folded about the body 336. Other contemplated embodiments include flexible covers, such as straps, strips, bands, and the like, which may not slide fully around the body 336. For example, some embodiments include spools for winding the flexible covers for storage and control thereof.

Still referring to FIGS. 5A and 5B, the cover 320 is designed with a series of small holes 358 that are in coded sequences, readable by a sensor. The coded sequences vary at different positions on the cover 320, such that detection of a portion of the coded sequence by the sensor provides positional information to the controller of the cover 320 orientation relative to the body 336. Still other embodiments count rotations of one of the rollers 332 to determine the position of the cover 320 relative to a starting position thereof. In some embodiments, holes may be noncircular, such as diamond-shaped, teardrop shaped, or otherwise shaped. Including a corner (e.g., crack initiation location, vertex) to the shape of the holes may improve tamper evidence by facilitating a controlled tearing of the cover if unauthorized, forced entry is attempted.

The rollers 332 are positioned on the longitudinal ends of the insert 318, where at least one of the rollers 332 is in the form of a sprocket 360 (with teeth). In such embodiments, the cover 320 includes perforated tracks 338. The teeth of the sprocket 360 fit the perforations 346, such that the cover 320 is moved relative to the body 336 via controlled rotation of the sprocket 360. In other embodiments, rollers 332 have a high-friction surface, such as sandpaper grit or a gripping rubber, for providing force to move the cover 320, without teeth. The rollers 332 may be injection molded from Celcon or Delrin materials, cast or molded metals, and/or composites.

Figure 6:
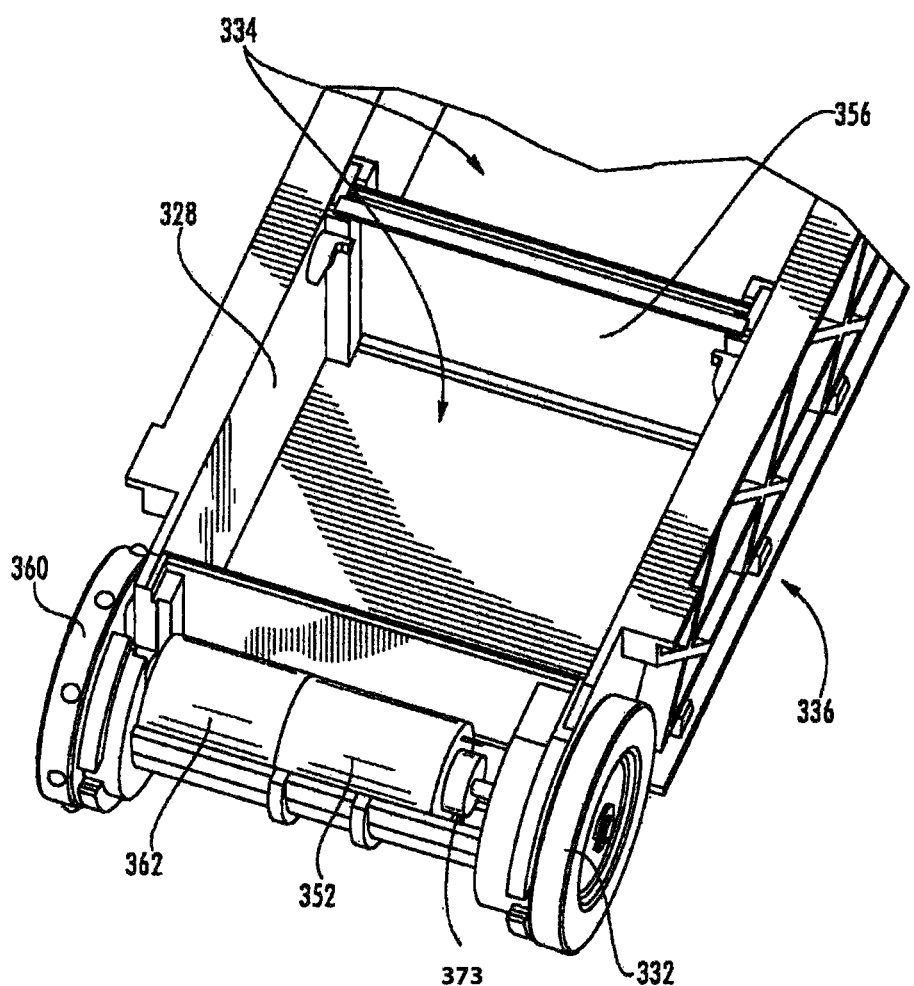
FIG. 6 is a perspective view of a portion of the drawer unit of FIG. 5.

FIG. 6 further illustrates the side walls 328, a removable divider wall 356, rollers 332 (one being a sprocket 360), the electric motor 352, and a gear reduction 362. The electric motor 352 (e.g., direct current motor) is coupled to the gear reduction 362, which in turn is coupled to the sprocket 360, coupled to the cover 320. According to an exemplary embodiment, the electric motor 352 is selectively powered by the controller via a power/data bus coupled to the insert 318, and selectively connected to a power source when the drawer unit 312 is locked within the cabinet housing.

The inserts 318 of FIGS. 5A and 5B may additionally include a data storage device coupled to the power/data bus. In some embodiments, the data storage device is coupled to the electric motor 352 (illustrated in FIG. 6). Manual sliding of the cover 320 forces the electric motor 352 to operate in reverse, generating an electric signal that is transmitted on the power/data bus. Data representative of the electric signal is stored on the data storage device 373. In other embodiments, the data storage device 373 is a mechanical detection device, such as a spring-loaded interlock. Manual sliding of the cover 320 triggers the interlock, which locks the cover 320 and may additionally trigger an alarm.

Figure 7:
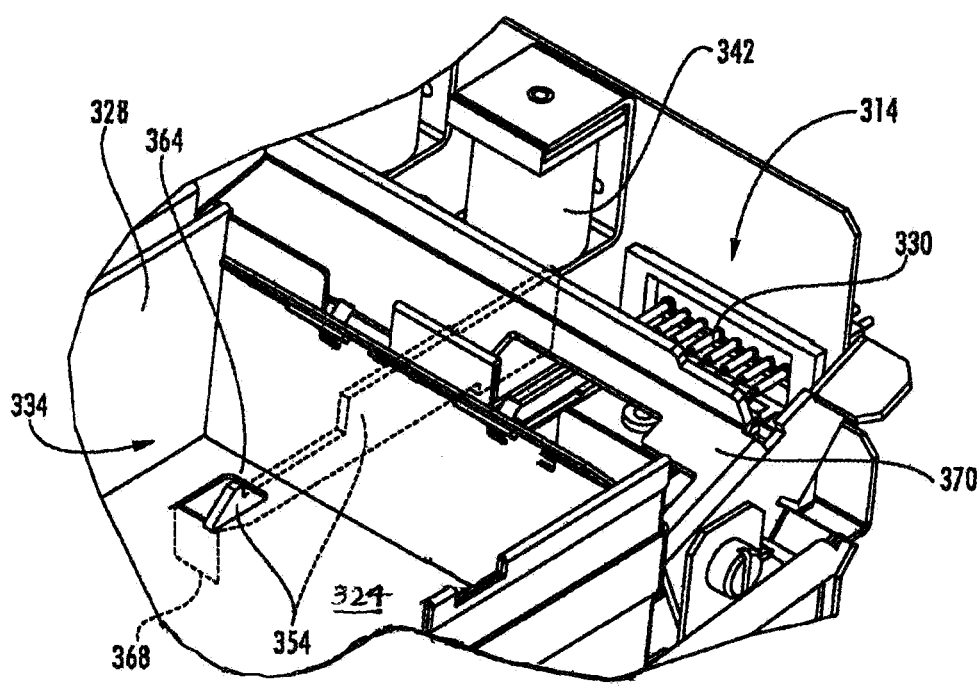
FIG. 7. is a perspective view of a portion of the cabinet system of FIG. 3.

Referring now to FIG. 7, the shell 324 may be locked to the rear portion 314 of the cabinet housing by a latch 354. The latch 354 extends beneath the shell 324 and connects to the shell 324 via a strike 364 (e.g., reinforced hole, catch) coupled to the shell 324. The latch 354 is coupled with the actuator 342, which is coupled by the controller to selectively release the shell 324. A security deflection tab 366 (e.g., "fishability bracket"), as shown in FIG. 4, may serve to block attempts to manipulate the latch 354 from an above position, such as by drilling a hole in the top of the cabinet housing and reaching down through the hole with a rod to release the latch 354. A second tab 368 extends from the shell 324 to block attempts to manipulate the latch 354 from the front of the cabinet housing. A manual release plate 370 allows for release of the drawer units 312 by key, code, etc., during a power outage (e.g., manual key override).

Figure 8:
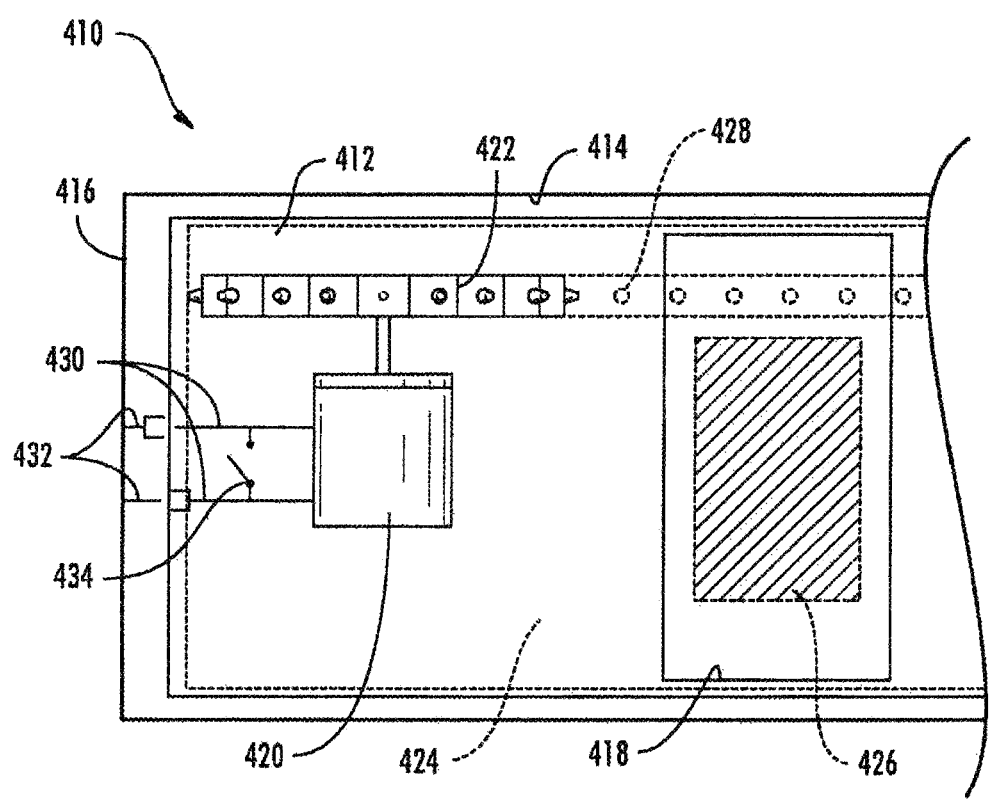
FIG. 8 is a schematic view of a portion of a cabinet system according to an exemplary embodiment of the invention.

Referring now to FIG. 8, an alternative for the drawer, a drawer 412, includes at least one compartment 418 and an actuator (e.g., electric motor, solenoid, electromagnet pair, etc.) in the form of an electric motor 420, which is coupled to a sprocket 422. A cover 424 is coupled to the drawer 412 and is configured to selectively block access to the compartment 418. In some embodiments, the cover 424 is a belt that surrounds at least a portion of the drawer 412. An opening 426 in the cover may be aligned with the compartment 418 in the drawer 412. Alignment of the opening 426 of the cover 424 with the compartment 418 allows for access to items stored in the compartment 418 and while simultaneously preventing access to other compartments in drawer 412. Misalignment of the opening 426 of the cover 424 with the compartment 418 allows the cover 424 to block access to the items. The sprocket 422 is configured to engage a track 428 on the cover 424 to move the cover 424 (and the opening 426 therein) relative to the drawer 412 (and compartment 418 therein).

The electric motor 420 of the drawer 412 includes electric leads 430 (e.g., wires, conductive extensions, prongs, etc.) in electrical communication with the working components (e.g., rotor/stator portions) of the motor 420. The leads 430 are configured to engage couplings 432 associated with a housing 416. As such, when the drawer 412 in securely within the housing 416, the leads 430 of the motor 420 are in electrical communication with a power source connected through the housing 416. However, when the drawer 412 is slid from the enclosure (at least partially), the leads 430 are decoupled from the power source, breaking electrical connectivity to the motor 420. Accordingly, the motor 420 does not rotate the sprocket 422, and the cover 424 is not moved by the motor 420 when the drawer 412 is slid from an enclosure 414.

Still referring to FIG. 8, cabinet system 410 includes a locking mechanism for locking the cover 424 when the drawer 412 is slid from the housing 416, which includes a switch 434 (e.g., relay) extending between the leads 430 of the motor 420. According to an exemplary embodiment, the switch 434 is open when the drawer 412 is electrically coupled to the power source by way of the couplings 432 of the housing 416. However, when the drawer 412 is slid from the housing 416 and away from the couplings 432 breaking the electrical connectivity between the drawer 412 and the power source, the switch 434 is automatically closed, shorting the leads 430 of the electric motor 420. As such, the internal components of the motor 420 (e.g., rotator/stator, drive shaft, gear reduction, transmission, etc.) serve as an interlock, resisting manual movement of the cover 424 by an unauthorized user. One type of effective gear reduction for providing locking is a 90° worm-gear drive. (Not specifically shown.)

Shorting the leads 430 also may serve to prevent an unauthorized user from attaching a supplemental power source to the leads 430, to power the motor 420 (e.g., hotwire the motor 420). As such, the switch 434 and electric motor 420, as coupled to the cover 424 by way of the sprocket 422, serve as a locking mechanism (e.g., brake) for the cover 424 when the drawer 412 is removed from the cabinet housing 416. In some embodiments, the motor 420 will generate electricity (e.g. a voltage and/or current) when manually operated in reverse, the occurrence of which may be recorded in an electric memory as evidence of tampering.

Figure 9:
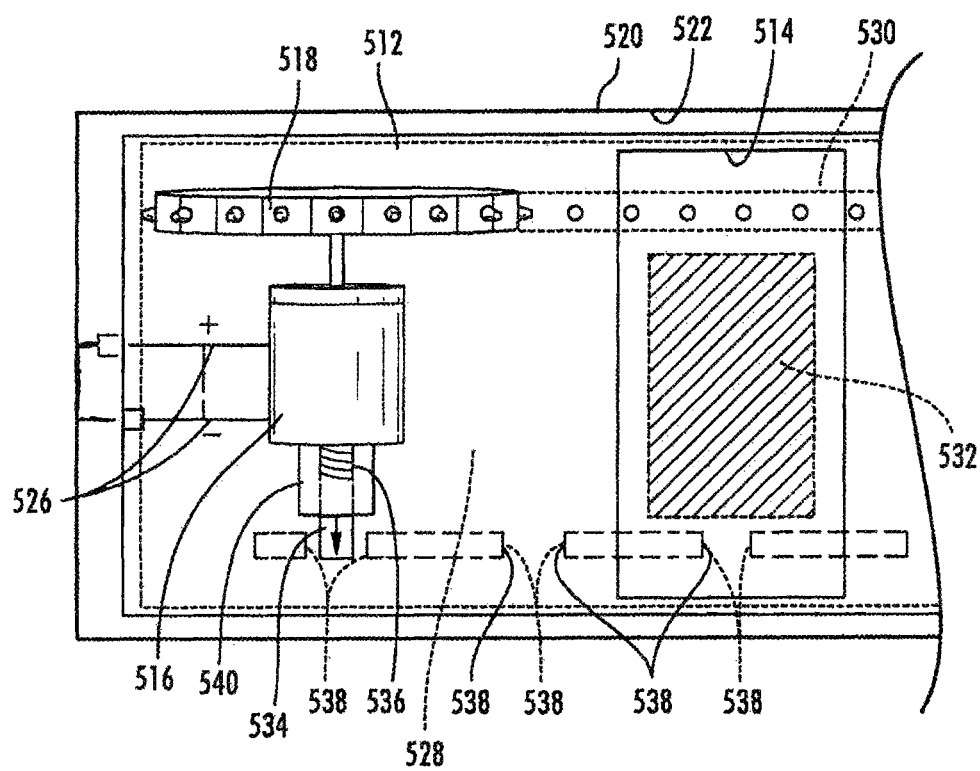
FIG. 9 is a schematic view of a portion of a cabinet system according to another exemplary embodiment of the invention.

Referring now to FIG. 9, another alternative of the drawer, drawer 512, also has a compartment 514 and an electric motor 516 coupled to a sprocket 518. The cover 528 is movable by the electric motor 516 via rotation of the sprocket 518 which engages a track 530 on the cover 528. Movement of the cover 528 provides selective access to items stored in the compartment 514 of the drawer 512 by way of an opening 532 in the cover.

A locking mechanism in the form of a pin 534 may be used to lock the cover 528 relative to the drawer 512 (and the compartment 514 therein). The pin 534 may be biased by a spring 536 and may interlock the cover 528 when the drawer 512 is slid from the housing 520. Sliding the drawer 512 from the housing 520 may release the pin 534 from being held in place by the housing 520, releasing tension on the spring 536, which slides the pin 534 into a corresponding slot 538 in the cover 528. When the drawer 512 is returned to the housing 520, the housing 520 reengages the pin 534, removing the pin 534 from the slot 538 and unlocking the cover 528. In some embodiments, the pin 534 may be used in conjunction with a switch selectively coupling the leads 526 (see, e.g., switch 434 as shown in FIG. 8).

The pin 534 may also be positioned within an electromagnet 540 (e.g., acting as solenoid), and is biased by the spring 536 in opposition to electromagnetic forces on the pin 534 selectively provided by the electromagnet 540. When electricity is supplied to the electromagnet 540, the pin 534 is pulled against the spring 536, compressing the spring 536. When electricity is not supplied to the electromagnet 540, the spring 536 is released, pushing the pin 534 forward to engage and lock the cover 528 in the slot 538 (e.g., hole) therein. When the drawer 512 is returned to the housing 520 and electricity is restored to the electromagnet 540, the pin 534 is pulled from the slot 538 of the cover 528, releasing the cover 528 to move relative to the compartment 514. In some embodiments, a manual override key (e.g., physical key, push button code, etc.) may be used to release the cover 528 from the pin 534 when the drawer 512 is out of the enclosure 522. In other embodiments, a clamp coupled to the pin 534 may be used to selectively grip the cover, in place of engagement with the slot 538.

Figure 10:
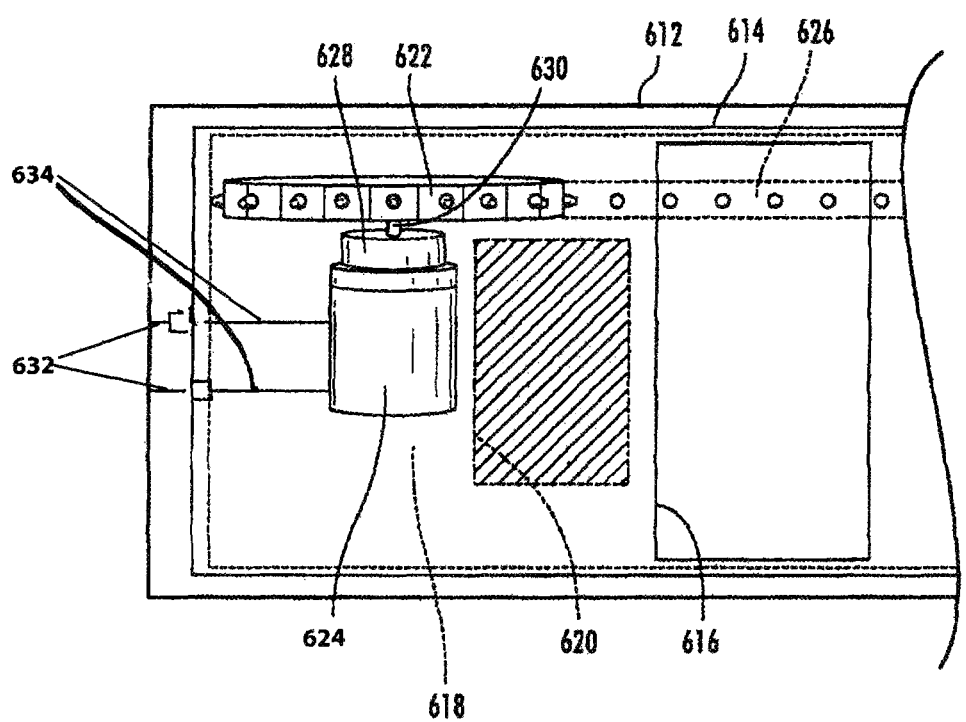
FIG. 10 is a schematic view of a portion of a cabinet system according to yet another exemplary embodiment of the invention.

Referring now to FIG. 10, another version of the drawer, drawer 614, is shown. As with the other versions, drawer 614 includes several compartments 616 for storage of medical items. A cover 618 having an opening 620 therein is coupled to the drawer 614, and moveable relative to the compartments 616 of the drawer 614 via a sprocket 622 coupled to a motor 624, the sprocket 622 engaging a track 626 on the cover 618.

A locking mechanism in the form of a motor brake 628 (e.g. function brake or jaw brake) is coupled to the motor 624. According to an exemplary embodiment, the motor brake 628 is configured to lock a shaft 630 of the motor 624 when electrical power is cut to the motor brake 628. A power source is coupled to the drawer 614 by way of couplings 632 of the housing 612 that may be selectively connected to leads 634 of the motor 624 and to the motor brake 628 of the drawer 614. When the drawer 614 is pulled from the cabinet housing 612, electricity to the drawer 614 is cut and the cover 618 is locked relative to the compartments 616 of the drawer 614. When the drawer 614 is returned to the cabinet housing 612 and electricity is restored to the motor brake 628, the cover 618 is released and may be moved (by way of the motor 624 and sprocket 622) relative to the compartments 616 of the drawer 614 to block or allow access to items stored therein.

Figure 11:
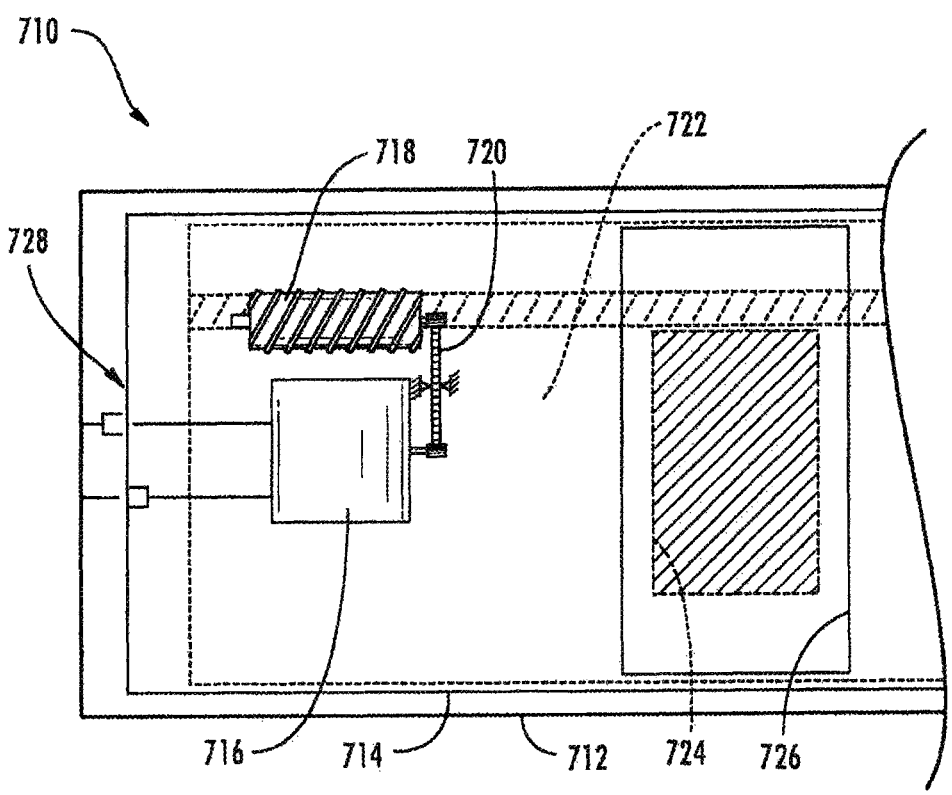
FIG. 11 is a schematic view of a portion of a cabinet system according to still another exemplary embodiment of the invention.

Referring to FIG. 11, another version of the drawer, drawer 714, is shown. In this version, an electric motor 716 is powered via an electric coupling 728 with the housing 712 driving a worm gear 718 by way of intermediate gearing 720 is configured to control movement of a cover 722 that includes an opening 724 that is adjustable to selectively block access to contents stored in a compartment 726 of the drawer 714. When the drawer 714 is within the cabinet housing 712, the drawer 714 is electrically coupled to a power source, and the motor 716 controls rotation of the worm gear 718 to move the cover 722. However, when the drawer 714 is removed (or at least partially removed) from the cabinet housing 712, electrical connectivity between the drawer 714 and the power source is severed. The worm gear 718 and motor 716 serve as an interlock, preventing manual movement of the cover 722 by an unauthorized user attempting to gain access to items stored in a compartment 726 of the drawer 714 that is intended by a controller of the cabinet system 710 to be closed.

Although electrical connectivity in FIGS. 8-11 is shown as a coupling of leads of the electric motors connected to leads extending from the cabinet housing, in other embodiments the power source or a portion of the power source may be coupled to a drawer even when the drawer is pulled from the cabinet housing. Movement of the drawer, or relative position of the drawer may trigger actuation of a combination of the locking mechanisms of FIGS. 8-11. Additionally, alternative locking mechanisms that are commercially available, may be used in combination with the or in place of the locking mechanisms shown in FIGS. 8-11, to control access to items securely stored in the drawers.

Figure 12:
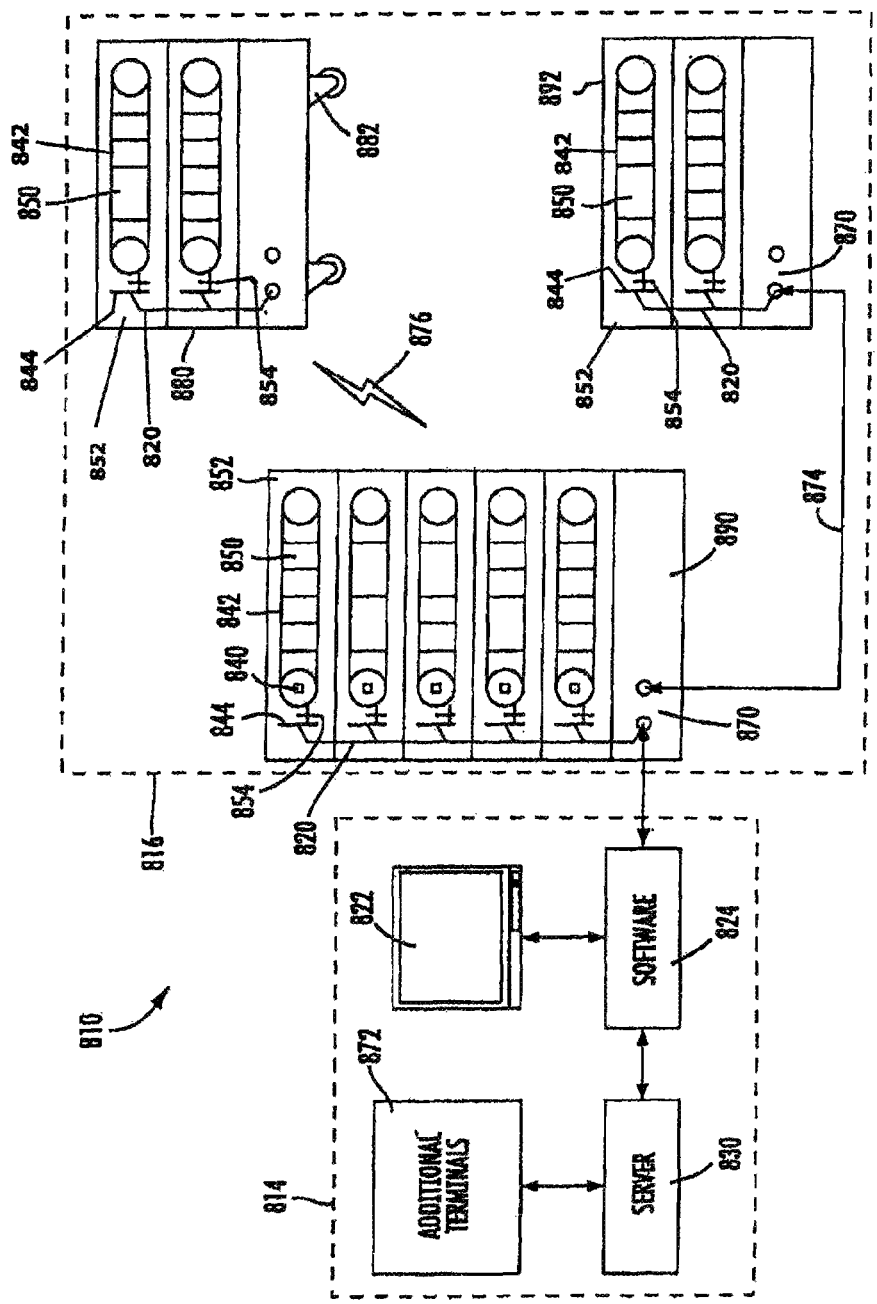
FIG. 12 is a block diagram of an item management system.

Referring now to FIG. 12, a cabinet system 810 (e.g., item management system, controlled-access medication dispensing system) includes cabinet hardware 816 including a first stationary cabinet 890, a second stationary cabinet 892 that is smaller than the first stationary cabinet 890, and a portable cabinet 880 (e.g., including wheels or casters 882). The first and second stationary cabinets 890, 892 are linked together via a communication wire 874, while the first stationary cabinet 890 is linked with the portable cabinet 880 via wireless communication 876 (e.g., RF). In some embodiments, the first and second stationary cabinets 890, 892 include structure for coupling the cabinets 890, 892 together, either side-by-side or one on top of the other.

The cabinet system 810 further includes a computerized controller 814 (e.g., electronic control system), which includes a user interface 822 (e.g., terminal) and a computer 824 having a processor, memory, and a logic module. According to an exemplary embodiment, the computerized controller 814 may further or otherwise include a server 830 and additional computers and terminals 872. As shown in FIG. 12, the computerized controller 814 is connected to an interface 870 on the first stationary cabinet 890, and is also connected to the second stationary cabinet 892 and the portable cabinet 880 by way of the first stationary cabinet 890 (e.g., daisy-chain arrangement). In other embodiments, the controller 814 is directly connected to the second stationary cabinet 892 and the portable cabinet 880.

Each of the cabinets 890, 892, 880 include one or more drawer units 850 that are slidable within housings 852 (e.g., bays, enclosures) of the cabinets 890, 892, 880. The system 810 may also include a locking connector 854 (e.g., a latch) that selectively locks the drawer units 850 within the housing 852. According to an exemplary embodiment, the interfaces 870 connect the controller 814 via a bus 820 to sensors 844, the locking connector 854, and other components within the housing 852. The drawer units 850 are locked within the housings 852 of the cabinets 890, 892, 880 until released by the computerized controller 814.

Each of the drawer units 850 include one or more compartments formed therein (shown as large and small boxes in each drawer unit 850), within which items may be securely stored. Covers 842 are coupled to the drawer units 850. Sensory data from the sensors 844 allows the controller 814 to estimate a position of the covers 842. The covers are designed to selectively block access to the compartments when the drawer units 850 have been slid from the housing 852. According to an exemplary embodiment, when a drawer unit 850 is within the housing 852 of one of the cabinets 890, 892, 880, the computerized controller 814 may instruct an actuator 840 coupled to one of the drawer units 850 to move the respective cover 842 relative to the drawer unit 850. When the an opening in the cover 842 is aligned with a designated compartment, the compartment may be accessed by an authorized operator of the system 810 when the drawer unit 850 has been slid from the housing 852.

A number of embodiments of the drawer units have been described above in reference to the figures (e.g. FIGS. 5A, 5B, 6, and 8-11). For tensioning the belts used with these units, various forms of belt tensioning may be used. One example is to provide fixed rollers/sprockets 332 on each end of the belt with an adjustable idler roller or slide to tension the belt. Another example is to provide a tensioning assembly which is configured to permit both removal and tensioning of the belt relative to a drawer unit. This is accomplished by supporting the shaft of at least one of the belt rollers/sprockets 332 with bearings which are adjustable relative to the frame of the drawer unit. This form of adjustment includes having the bearings slidably mounted on slides which permit movement of the roller along a path generally parallel to the length of the belt. The slides are moved with adjustment screws or bolts and can be held in place with set screws.

Figure 13:
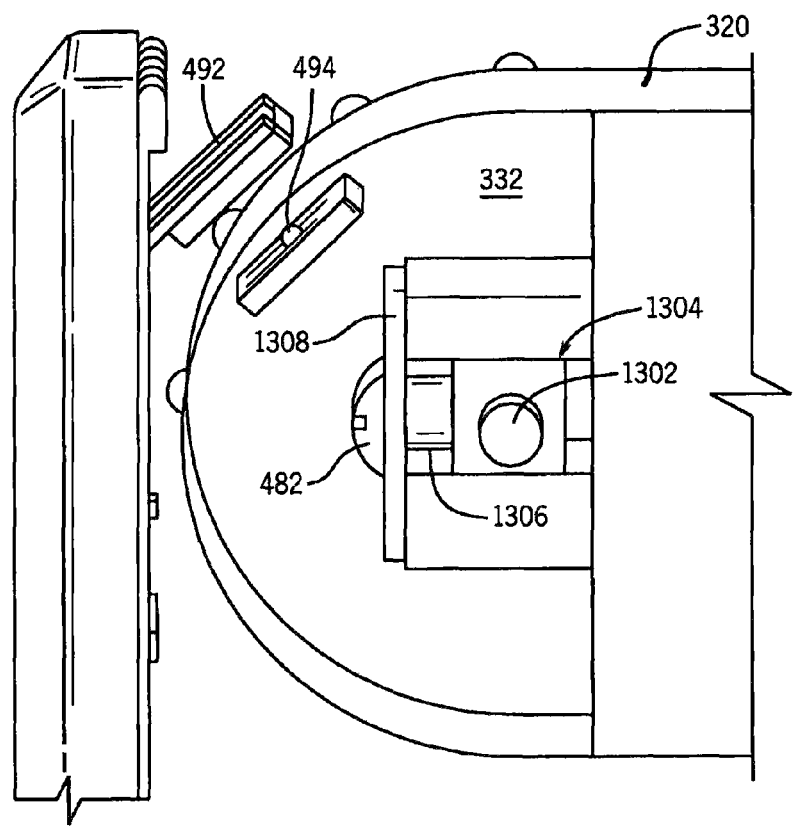
FIG. 13 is a schematic illustration of a belt tension adjustment arrangement and a sensor assembly.

FIG. 13 schematically illustrates a form of the second example of the tension adjustment discussed. In particular, each side of the roller shaft 1302 is supported by a slide assembly 1304. A bolt 482 is engaged with a threaded portion of the sliding portion of assembly 1304. The head of bolt 482 rests against an adjustment stop 1308 so that when bolt 482 is turned into the threaded portion, the belt 320 (also referred to as cover) is tightened. By providing tension adjustment at both ends of the roller shaft 1302, the belt 320 can be tightened and adjusted so that the belt 320 is not biased to tend to move off of the rollers 332.

FIG. 13 also shows a sensor assembly which includes an optical sensor 492 attached to a back wall a cabinet housing proximate to the back side of a drawer unit. The assembly also includes light source 494 (e.g. LED) which directs light from the interior of belt through openings 358 (see FIGS. 5A and 5B) of belt 320 toward sensor 492. The sensor assembly provides belt orientation information to controller 214 (see FIG. 2), so that the controller 214 may operate the motor 352 (see FIG. 6) (or other actuator) in relation to a current and/or desired orientation of the belt 320. As discussed, openings 358 are either uniformly spaced to provide uniform light interruptions which generate interrupt signals to the controller which are interpreted by the controller to determine the location of the belt openings relative to the compartments. This is done typically with the use of an initial position which has a unique light interruption, and then counting of interrupt signals from the initial position. Alternatively, the openings 358 may be patterned such that sensor 492 generates a signal representative of the pattern of openings 358 detected when light is transmitted through the belts. These signals are transmitted to the controller 214 which interprets the signals to determine the location of the belt openings relative to the compartments based on the coded patterns that vary at different positions on the belt 320. Detection of a particular coded sequence by the sensor 492 provides positional information.

Figure 14:
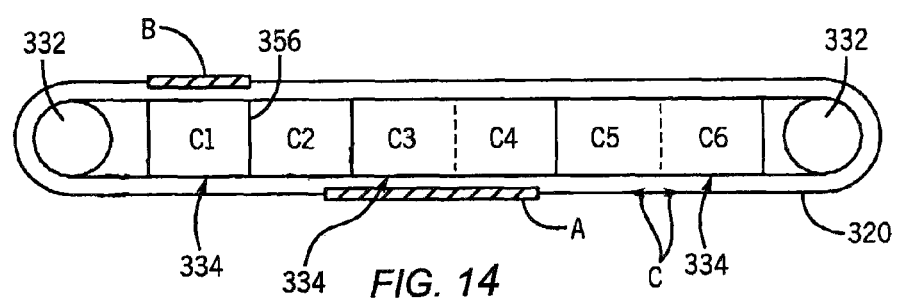
FIG. 14 is a schematic view of the compartments of a drawer unit in reference to a belt cover.

Referring to FIG. 14, a side schematic view of a drawer unit having a 3 compartments arranged end to end from a first end to a second end. One of the compartments is divided in half to form 2 half-size compartments. The belt rollers 332 supported at each end of the belt 320 are also schematically shown in combination with belt 320. Belt 320 has 2 openings which are schematically marked as A and B. Opening B is sized to correspond to the size of a half-size compartment. A belt actuator which includes a motor such as motor 352 (see FIG. 6) moves the belt 320 to align one of the openings A or B with the opening of a compartment 334 which includes a desired item such as a particular medication. By properly aligning an opening in the belt with the opening of one compartment, the remainder of the belt serves to restrict access to the other compartments of the drawer unit when the user slides the drawer unit from the associated cabinet.

As discussed above, the belt 320 is moved to align an opening A, B in the belt 320 with the opening in a compartment when the drawer unit is located within the cabinet. Accordingly, when a cabinet user requests a particular item, the actuator operates to move the belt 320 to provide access to the compartment having the requested item. Initiating and completing this operation must be done in the shortest period of time within which the system is capable of operating. The speed of operation is limited by the belt, drawer unit, actuator, and other drawer structure parameters. Accordingly, for a given set of parameters operation of the belt must be optimized.

In the preferred embodiment, the belt actuator is configured so that the belt 320 may be moved in both directions. As shown in FIG. 14, arrows C illustrate belt motion in either the clockwise or counter-clockwise directions. After a particular item is requested, the drawer unit is pulled from the cabinet, the item is removed, and the drawer is returned, the openings A and B typically remain in the position the had prior to item removal. Depending upon the frequency with which compartments are accessed, controller 214 may be programmed/configured to move the belt 320 so that upon the next item request the most probably distance of belt travel is reduced. When using a belt 320 as the compartment cover, the distance of travel or movement is defined as either the time or physical distance the belt must travel to move either opening A or opening B over the opening of the compartment 334 which contains a selected item. As shown in FIG. 14, the distance of travel will typically be different depending upon the direction of travel (e.g. clockwise or counter-clockwise). By way of specific example, when belt 320 is positioned as shown in FIG. 14, the distance of travel in the clockwise direction required to move opening B over compartment C6 is much less than the distance of travel in the counter-clockwise direction. Accordingly, controller 214 is programmed to keep track of belt 320 opening A, B positions relative to compartments C1-C6, and to select the direction of travel to minimize the distance of travel.

Controller 214 may also be programmed to keep track of the frequency at which items in the compartments C1-C6 are accessed and position the belt 320 when the drawer unit is not in use to increase the likelihood that belt travel will be minimized. By way of specific example, if the drawer unit is accessed 100 times, and the majority of these time compartments C1 and C3 are accessed, controller 214 would position belt 320 so that opening B was located generally in the vicinity of compartments C1 and C3 when the drawer is returned and locked in the cabinet and not in use. This would result in opening B being positioned over approximately over compartment C2 depending upon whether or not the speed of belt movement available from the actuator is designed for a particular application to be the same in both directions.

The construction and arrangements of cabinet system, as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A secured cabinet comprising:
a drawer housing;
a plurality of drawer units slidable within the drawer housing between an extended position and a retracted position, each of the plurality of drawer units comprising:
a top frame having an opening;
a shell coupled to the top frame, the shell having receiving portions;
an insert disposed between the top frame and the shell, the insert having an interior divided into at least a first compartment and a second compartment and flanges extending from the insert and contacting the receiving portions;
a belt having an opening, the belt being moveably supported by the insert and being moveable to align the opening with the opening in the top frame and with either the first compartment or the second compartment, wherein the contact of the flanges and the receiving portions separate the belt form the shell during movement;
a belt actuator supported by the insert and configured to move the belt; and
an electronic controller in communication with the belt actuators of each drawer unit, wherein the controller is configured to control the belt actuator of each drawer unit to move the belt of each drawer unit to provide access to the compartments of the drawer unit, wherein the controller, in response to a user request to access one of the compartments of one of the drawer units, is configured direct the belt actuator of the drawer unit to move the belt.

2. The secured cabinet of claim 1 further comprising a plurality of restraining devices coupled to the insert and configured to hold items within the first and second compartments.

3. The secured cabinet of claim 1 wherein the controller is configured to cause movement of the belt of each drawer unit only when the drawer unit is in the retracted position within the housing.

4. The secured cabinet of claim 1 wherein the movement of each belt is movement that occurs above the first compartment and the second compartment of the requested drawer unit.

5. The secured cabinet of claim 1 further comprising a first roller supported at a first end of each insert and a second roller supported at a second end of each insert.

* * * * *